United States Patent [19]
Fok et al.

[11] Patent Number: 5,821,267
[45] Date of Patent: Oct. 13, 1998

[54] AMIDINO DERIVATIVES USEFUL AS NITRIC OXIDE SYNTHASE INHIBITORS

[75] Inventors: Kam F. Fok, St. Louis; Foe S. Tjoeng, Manchester; R. Keith Webber, St. Peters, all of Mo.

[73] Assignee: G.D. Searle & Co., Chicago, Ill.

[21] Appl. No.: 604,972

[22] PCT Filed: Oct. 18, 1994

[86] PCT No.: PCT/US94/11724
§ 371 Date: Mar. 20, 1996
§ 102(e) Date: Mar. 20, 1996

[87] PCT Pub. No.: WO95/11014
PCT Pub. Date: Apr. 27, 1995

Related U.S. Application Data

[63] Continuation-in-part of Ser. No. 139,970, Oct. 21, 1993, abandoned.

[51] Int. Cl.$^6$ .................. A61K 31/155; A61K 31/44; A61K 31/38; A61K 31/34
[52] U.S. Cl. .................. 514/631; 514/637; 514/357; 514/438; 514/471; 514/633; 514/378
[58] Field of Search .................. 514/433, 631, 514/637, 357, 438, 471, 633, 375; 549/74

[56] References Cited

U.S. PATENT DOCUMENTS

| | | | |
|---|---|---|---|
| 3,445,517 | 5/1969 | Mills | 514/443 |
| 3,632,593 | 1/1972 | Gautier et al. | 514/443 |
| 4,713,369 | 12/1987 | Stüber | 514/18 |
| 5,059,712 | 10/1991 | Griffith | 562/560 |
| 5,081,148 | 1/1992 | Braquet et al. | 514/162 |
| 5,132,453 | 7/1992 | Griffith | 562/560 |
| 5,196,450 | 3/1993 | Sjoerdsma et al. | 514/565 |
| 5,273,875 | 12/1993 | Griffith | 435/1 |
| 5,281,627 | 1/1994 | Griffith | 514/565 |
| 5,350,770 | 9/1994 | Elford et al. | 514/575 |
| 5,362,744 | 11/1994 | Purchase, Jr. et al. | 514/381 |
| 5,364,881 | 11/1994 | Griffith et al. | 514/508 |
| 5,464,858 | 11/1995 | Griffith et al. | 514/399 |

FOREIGN PATENT DOCUMENTS

| | | |
|---|---|---|
| 0370320 | 5/1990 | European Pat. Off. . |
| 0446699 | 9/1991 | European Pat. Off. . |
| 2240041 | 7/1991 | United Kingdom . |
| 91/04023 | 4/1991 | WIPO . |
| 91/04024 WO | 4/1991 | WIPO . |
| 92/040504 | 3/1992 | WIPO . |
| WO 93/03714 | 3/1993 | WIPO . |
| 93/13055 | 7/1993 | WIPO . |
| 93/16721 | 9/1993 | WIPO . |
| 93/24126 | 12/1993 | WIPO . |
| WO 94/02135 | 2/1994 | WIPO . |
| 93/14780 | 7/1994 | WIPO . |
| 95/00505 | 1/1995 | WIPO . |
| 95/11014 | 4/1995 | WIPO . |
| 96/06076 | 2/1996 | WIPO . |

OTHER PUBLICATIONS

Gould et al., "Nucleoside Intermediates in Blasticidin S Biosynthesis Identified by the In Vivo Use of Enzyme Inhibitors", *Can. J. Chem.*, vol. 72, pp. 6–11, 1994.

Tsunematsu et al., "β–Naphthylamides of Guanidinophenyl Amino Acids as Substrates of Aminopeptidases", *Chem. Pharm. Bull.*, vol. 36, No. 3, pp. 1205–1209, 1988.

Funabashi et al., "A New Anti–MRSA Dipeptide, TAN–1057 A", *Tetrahedron*, vol. 49, No. 1, pp. 13–28, 1993.

Prabhakaran et al., "Studies on Nitrogen Metabolism Using $_{13}$C NMR Spectroscopy. 5.$_1$ Metabolism of L–α–Arginine in the Biosynthesis of Blasticidin S", *Tetrahedron*, vol. 27, No. 33, pp. 3815–3818, 1986.

Stuehr et al., "Mammalian Nitric Oxide Synthases", *Advances in Enzymology*, vol. 65, 1992, (p. 317).

Plapp et al., "Determination of ε–Acetimidyllysine in Proteins" *Analytical Biochemistry*, vol. 62, pp. 291–294, 1974.

Rees et al., "Characterization of Three Inhibitors of Endothelial Nitric Oxide Synthase in vitro and in vivo", *Br. J. Pharmacol.*, vol. 101, pp. 746–752, 1990.

Proudfoot et al., "Conformation–directed Recombination of Enzyme–activated Peptide Fragments: A Simple and Efficient Means to Protein Engineering", *J. Bio. Chem.*, vol. 264, No. 15, pp. 8764–8770, 1989.

Palacios, et al., "Nitric Oxide from L–Arginine Stimulates the Soluble Guanylate Cyclase in Adrenal Glands", *Biochemical and Biophysical Research Communications*, vol. 165, No. 2, pp. 802–809, 1989.

Knowles et al., "Kinetic Characteristics of Nitric Oxide synthase from Rat Brain", *Biochem. J.*, vol. 269, pp. 207–210, 1990.

CA 107, 40336y, 1987.
CA 63, 5641d, 1965.
CA 97, 38442m, 1982.
CA 76, 43768t, 1972.
CA 118, 72838g, 1993.
CA 64, 17593h, 1966.
CA 115, 29868t, 1991.
Ca 104, 202858, 1986.

*Primary Examiner*—Deborah C. Lambkin
*Attorney, Agent, or Firm*—Dennis Bennett; Alan L. Scrivner

[57] ABSTRACT

The current invention discloses amidino derivatives useful as nitric oxide synthase inhibitors.

12 Claims, No Drawings

AMIDINO DERIVATIVES USEFUL AS NITRIC OXIDE SYNTHASE INHIBITORS

This application is a 371 of PCT/US94/11724 filed Oct. 18, 1994 and a CIP of 08/139,970 filed Oct. 21 1993, abandoned.

BACKGROUND OF THE INVENTION

1. Field of the Invention

The present invention relates to amidino derivatives and their use in therapy, in particular their use as nitric oxide synthase inhibitors.

2. Related Art

It has been known since the early 1980's that the vascular relaxation brought about by acetycholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amylnitrite, glyceryltrinitrite and other nitrovasodilators. The recent identification of EDRF as NO has coincided with the discovery of a biochemical pathway by which NO is synthesized from the amino acid L-arginine by the enzyme NO synthase.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al. *Biochemical Pharmacology*, 38, 1709–1715 (1989) and Moncada et al. *Pharmacological Reviews*, 43, 109–142 (1991). It is now thought that excess NO production may be involved in a number of conditions, particularly conditions which involve systemic hypotension such as toxic shock and therapy with certain cytokines.

The synthesis of NO from L-arginine can be inhibited by the L-arginine analogue, L-N-monomethyl-arginine (L-NMMA) and the therapeutic use of L-NMMA for the treatment of toxic shock and other types of systemic hypotension has been proposed (WO 91/04024 and GB-A-2240041). The therapeutic use of certain other NO synthase inhibitors apart from L-NMMA for the same purpose has also been proposed in WO 91/04024 and in EP-A-0446699.

It has recently become apparent that there are at least three types of NO synthase as follows:

(i) a constitutive, $Ca^{++}$/calmodulin dependent enzyme, located in the endothelium, that releases NO in response to receptor or physical stimulation.

(ii) a constitutive, $Ca^{++}$/calmodulin dependent enzyme, located in the brain, that releases NO in response to receptor or physical stimulation.

(iii) a $Ca^{++}$ independent enzyme which is induced after activation of vascular smooth muscle, macrophages, endothelial cells, and a number of other cells by endotoxin and cytokines. Once expressed this inducible NO synthase synthesizes NO for long periods.

The NO released by the constitutive enzymes acts as a transduction mechanism underlying several physiological responses. The NO produced by the inducible enzyme is a cytotoxic molecule for tumor cells and invading microorganisms. It also appears that the adverse effects of excess NO production, in particular pathological vasodilation and tissue damage, may result largely from the effects of NO synthesized by the inducible NO synthase.

There is also a growing body of evidence that NO may be involved in the degeneration of cartilage which takes place in certain conditions such as arthritis and it is also known that NO synthesis is increased in rheumatoid arthritis. Accordingly, further conditions in which there is an advantage in inhibiting NO production from L-arginine include autoimmune and/or inflammatory conditions affecting the joints, for example arthritis.

Conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy. Further conditions in which there is an advantage in inhibiting NO production from L-arginine include autoimmune diseases and/or inflammatory conditions such as those affecting the joints, for example arthritis or inflammatory bowel disease, cardiovascular ischemia, diabetes, hyperalgesia (allodynia) cerebral ischemia (Both focal ischemia, thrombotic stroke and global ischemia, secondary to cardiac arrest) and other CNS disorders mediated by NO.

Some of the NO synthase inhibitors proposed for therapeutic use so far, and in particular L-NMMA, are non-selective in that they inhibit both the constitutive and the inducible NO synthase. Use of such a non-selective NO synthase inhibitor requires that great care be taken in order to avoid the potentially serious consequences of over-inhibition of the constitutive NO-synthase including hypertension and possible thrombosis and tissue damage. In particular, in the case of the therapeutic use of L-NMMA for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive NO synthase would be of even greater therapeutic benefit and easier to use.

WO 94/12165, WO 94/14780, Wo93/13055, EP 0446699A1 and U.S. Pat. No. 5,132,453 disclose compounds that inhibit nitric oxide synthesis and preferentially inhibit the inducible isoform of nitric oxide synthase. The disclosures of which are hereby incorporated by reference in their entirety as if written herein.

SUMMARY OF THE INVENTION

In a broad aspect, the present invention is directed to inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase. It is also another object of the present invention to lower nitric oxide levels in a subject in need of such lowering.

The invention relates a method of inhibiting nitric oxide synthesis in a subject in need of such inhibition by administering a therapeutically effective amount of a compound having the formula:

and salts, and pharmaceutically acceptable ester and prodrugs thereof, wherein:

A is hydrogen, lower alkyl, lower alkenyl, lower alkynyl group, alkylthioalkyl group, alkyloxyalkyl group, alkylsulfonylalkyl group, cycloalkyl group, bicycloalkyl group, cycloalkenyl group, cycloalkylalkyl group, phenylalkyl group, phenylalkenyl group, biphenylalkyl group, heterocyclic group, aryl substituted heterocyclic groups, biaryl group, or aryl wherein each said radical may optionally be substituted by one or more of the following substituents such as alkyl, alkoxy, hydroxy, halogen, nitro, cyano, haloalkyl, carboxylic, carboxamide, amino, alkylamino or dialkylamino; and R is H, OH or lower alkyl group.

The invention further relates to pharmaceutical compositions comprising a compound of formula (I) for use in the above method. Such compounds and compositions have usefulness as inhibitors of nitric oxide synthase. Conditions in which there is an advantage in inhibiting NO production include systemic hypotension associated with septic and/or toxic shock induced by a wide variety of agents, therapy with cytokines such as TNF, IL-1 and IL-2; autoimmune and/or inflammatory diseases affecting the joints such as arthritis, diabetes and inflammatory bowel disease.

Compounds and compositions defined above have usefulness as inhibitors of nitric oxide synthase. These compounds also prefentially inhibit the inducible form over the constitutive form by at least 3 fold.

DETAILED DESCRIPTION OF THE INVENTION

A preferred embodiment oF the present invention is a method using a pharmaceutical composition including a compound of the formula (I)

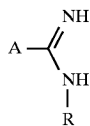

A is hydrogen, lower alkyl of 1 to about 10 carbon atoms, lower alkenyl group of 2 to about 6 carbon atoms, lower alkynyl group of 2 to about 6 carbon atoms, alkylthioalkyl group of 2 to about 6 carbon atoms, alkyloxyalkyl of 2 to about 6 carbon atoms, alkylsulfonylalkyl group of 2 to about 6 carbon atoms, cycloalkyl group of 3 to about 8 carbon atoms, bicycloalkyl group of 6 to about 10 carbon atoms, cycloalkenyl group of 3 to about 8 carbon atoms, cycloalkylalkyl group of 4 to about 10 carbon atoms, phenylalkyl group, phenylalkenyl group, biphenylalkyl group, heterocyclic group, or aryl substituted heterocyclic groups and which each group may be optionally be substituted by one or more of the following substituents: lower alkyl of 1 to about 4 carbon atoms, alkoxy of 1 to about 4 carbon atoms, hydroxy, halogen, nitro, cyano, haloalkyl, carboxyl, carboxamide, amino, monoalkylamino or dialkylamino; and R is H, OH or lower alkyl group of 1 to about 6 carbon atoms.

Another preferred embodiment of the present invention is a compound of the formula (I)

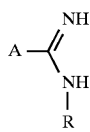 (I)

A is lower alkyl of 2 to about 10 carbon atoms, lower alkenyl of 2 to 6 carbon atoms, cycloalkyl group of 3 to 8 carbon atoms, bicycloalkyl group of 7 carbon atoms, alkylthioalkyl group of 2 to about 6 carbon atoms, alkyloxyalkyl of 2 to about 6 carbon atoms, alkylsulfonylalkyl group of 2 to about 6 carbon atoms, heterocyclic group, or aryl substituted heterocyclic group and which each may be optionally be substituted by one or more of the following lower alkyl, alkoxy, haloalkyl or halogen, nitro; and R is H, OH or lower alkyl group of 1 to about 6 carbon atoms.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, ρ-toluenesulphonic, benzenesulphonic and isethionic acids. Salts of the compounds of formula (I) can be made by reacting the appropriate compound in the form of the free base with the appropriate acid.

While it may be possible for the compounds of formula (I) to be administered as the raw chemical, it is preferable to present them as a pharmaceutical formulation. According to a further aspect, the present invention provides a pharmaceutical formulation comprising a compound of formula (I) or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of the invention may be administered orally or via injection at a dose of from 0.1 to 500 mg/kg per day. The dose range for adult humans is generally from 5 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As utilized herein, the term "lower alkyl", alone or in combination, means an acyclic alkyl radical containing from 1 to about 20, preferably from 1 to about 10 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 20 carbon atoms, preferably from about 2 to about 10 carbon atoms and more preferably 2 to about 6 carbon atoms. Examples of suitable alkenyl radicals include propenyl, buten-1-yl, isobutenyl, penten-1-yl, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radical in so much as it contains one or more triple bonds, such radicals containing from about 2 to about 20 carbon atoms, preferably having from about 2 to about 10 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "heterocyclic radical" means a saturated or unsaturated cyclic hydrocarbon radical with 4 to about 10 carbon atoms, preferably about 5 to about 6; wherein 1 to about 3 carbon atoms are replaced by nitrogen, oxygen or sulfur. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, 2-imidazolinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazonyl, quinolinyl, and the like.

The term "Aryl" means an aromatic hydrocarbon radical of 4 to about 16 carbon atoms, preferably 6 to about 12 carbon atoms, more preferably 6 to about 10 carbon atoms. Examples of suitable aromatic hydrocarbon radicals include phenyl, naphthyl, and the like.

The terms "Cycloalkyl" or "cycloalkenyl" means an "alicyclic radical in a ring with 3 to about 10 carbon atoms, and preferably from 3 to about 6 carbon atoms. Examples of suitable alicyclic radicals include cyclopropyl, cyclopropylenyl, cyclobutyl, cyclopentyl, cyclohexyl, 2-cyclohexen-1-ylenyl, cyclohexenyl and the like.

The term "alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, iso-butoxy, sec-butoxy, tert-butoxy and the like.

The term "halogen" means fluorine, chlorine, bromine or iodine.

The term "prodrug" refers to a compound that is made more active in vivo.

As used herein, reference to "treatment" of a patient is intended to include prophylaxis.

All references, patents or applications, U.S. or foreign, cited in the application are hereby incorporated by reference as if written herein.

The invention is illustrated by the following examples. Some of the compounds disclosed are publicly available from the source cited. Additional compounds of this invention have been described in publications as indicated or have been fully described herein.

EXAMPLE 1

2-Methylsulfonylacetamidine hydrochloride

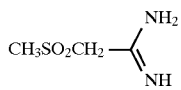

To a 250 mL flask was added 5 g (0.042 mol) of 2-methylsulfonylacetonitrile and 75 mL of anhydrous ethanol. This solution was cooled to 0° C. in an ice bath while anhydrous HCl was bubbled in until saturated. This mixture was allowed to warm very slowly with constant stirring over a 24 hour period. The reaction mixture was concentrated to a reduced volume, diluted with ethyl ether and filtered to afford 5.5 g of the ethyl imidate as a white solid. The imidate was added to 20 mL of anhydrous ethanol and cooled to 0° C. To this reaction mixture was added 80 mL of ethanol previously saturated with anhydrous ammonia. This mixture was capped and allowed to stir for three days. The reaction mixture was then concentrated to a reduced volume, diluted with ethyl ether and filtered to afford 4.7 g (65%) of the 2-Methylsulfonylacetamidine Hydrochloride as a white solid, mp 186°–194° C.

EXAMPLE 2

Cyclopropylcarbamidine; Lancaster Synthesis Inc.

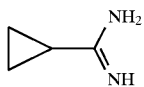

EXAMPLE 3

Isopropylcarbamidine; C. R. Hauser and C. J. Eby, J. Am. Chem. Soc. 79, 725–727 (1957).

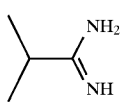

EXAMPLE 4

1-Propylcarbamidine; R. Almquist, R. A. Huggins and R. A. Woodbury, J. Pharmacol. 89, 271–288 (1947).

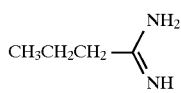

EXAMPLE 5

Ethylcarbamidine; ibid.

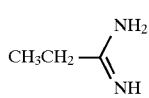

EXAMPLE 6

2-Methoxyacetamidine; BELG. 645062, 1964.

EXAMPLE 7

3-Amidinopyridine; Ryan Scientific.

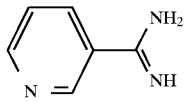

EXAMPLE 8

2-Amidinothiophene; Ryan Scientific.

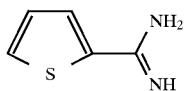

EXAMPLE 9

2-Amidinofuran; T. J. Schwan and K. O. Ellis, J. Pharm. Sci. 64(2), 337–338 (1975).

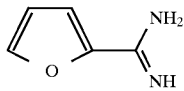

EXAMPLE 10

2-Chloroacetamidine; Transworld Chemical Inc.

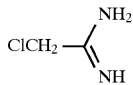

EXAMPLE 11

2-Methylmercaptoacetamide; GER. 2,928,185, F. Maurer and I. Hammann (1901).

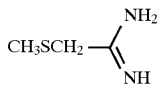

EXAMPLE 12

Isobutylcarbamidine hydrochloride; J. Gen. Chem. 14, 280–291 (1944)

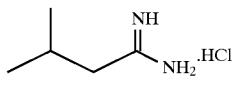

Prepared as in example 1 from isovalerylnitrile to afford the title compound as a white solid. 1H-NMR(D20) 0.9 (d, 6H), 2.05 (m, 1H), 2.25 (d, 2H); Mass Spectra, M+H=101; Elemental analysis Calcd. for C5H13N2C12+1/10 N1H4C11: C, 42.30; H, 9.51; N,20.72. Found C, 42.45, H, 9.47, N, 20.69.

EXAMPLE 13

Benzylthioacetamidine hydrochloride; Fr. 1,429,279

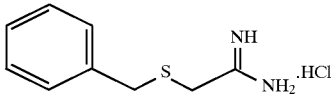

Prepared as in example 1 from benzylthioacetonitrile to afford the title compound as an off-white solid. 1H-NMR (D20) 3.35 (s, 2H), 3.73 (s, 2H), 7.22 (m, 5H); Mass Spectra, M+H=181.

EXAMPLE 14

Heptlycarbamidine hydrochloride; Chem. Abst. 41:5468i

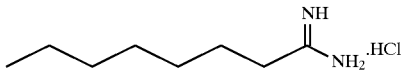

Prepared as in example 1 from heptylcyanide to afford the title compound as a white solid. Mass Spectra, M+H=143.

EXAMPLE 15

Heptadecylcarbamidine hydrochloride; J. Chem. Soc. 738–742 (1947)

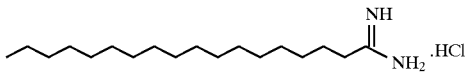

Prepared as in example 1 from heptadecylcyanide to afford the title compound as a white solid. Mass Spectra, M+H=283.

EXAMPLE 16

Undecylcarbamidine hydrochloride; Chem. Abst. 51:12808f

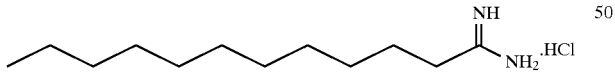

Prepared as in example 1 from undecylcyanide to afford the title compound as a white solid. Mass Spectra, M+H=199.

EXAMPLE 17

1-Bromo-6-carbamidylhexane hydrochloride Prepared as in example 1 from 1-bromo-6-cyanohexane to afford the title compound as a white solid. Mass Spectra, M+H=207.

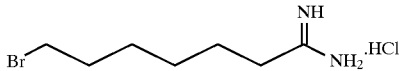

EXAMPLE 18

X-10191 1-Chloro-4-carbamidylbutane hydrochloride

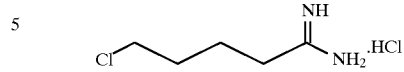

Prepared as in example 1 from 1-chloro-4-cyanobutane to afford the title compound as a white solid. Mass Spectra, M+H=135.

EXAMPLE 19

2-Carbamidyl-3-bromothiophene hydrochloride

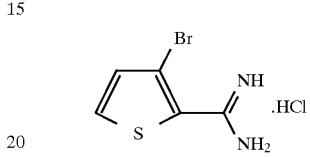

Prepared as in example 1 from 2-cyano-3-bromothiophene to afford the title compound as a white solid. Mass Spectra, M+H=205.

EXAMPLE 20

2-Amidyl, 3,4-dimethyl, 5-carbamidylthiophene hydrochloride

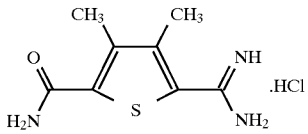

Prepared as in example 1 from 2-amidyl, 3,4-dimethyl, 5-cyanothiophene to afford the title compound as a white solid. Mass Spectra, M+H=198.

EXAMPLE 21

Styrylcarbamidine hydrochloride; J. Am. Chem. Soc. 78, 1434–7 (1956)

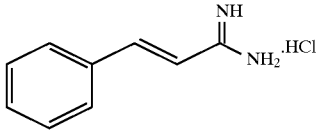

Prepared as in example 1 from cinnamonitrile to afford the title compound as a white solid. Mass Spectra, M+H=147.

EXAMPLE 22

2-carbamidylnorbornane hydrochloride

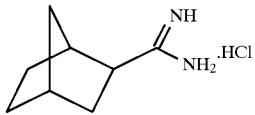

Prepared as in example 1 from 2-norbornanecarbonitrile to afford the title compound as a white solid. Mass Spectra, M+H=139.

EXAMPLE 23

2-Chloro-5-carbamidylnorbornane hydrochloride

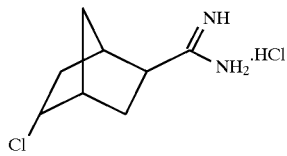

Prepared as in example 1 from 2-Chloro-5-cyanonorbornane to afford the title compound as a white solid. Mass Spectra, M+H=173.

EXAMPLE 24

2-Phenylbutyramidine hydrochloride; Compt. Rend. 246, 2905–6 (1958)

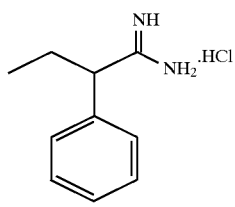

Prepared as in example 1 from 2-phenylbutyronitrile to afford the title compound as a white solid. Mass Spectra, M+H=163.

EXAMPLE 25

2,6-Dimethyl, 7-carbamidylhepta-2-6-diene hydrochloride

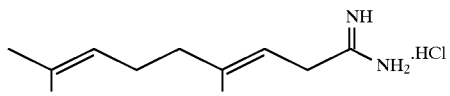

Prepared as in example 1 from 2,6-Dimethyl, 7-cyanohepta-2-6-diene to afford the title compound as a white solid. Mass Spectra, M+H=167.

EXAMPLE 26

2-Methyl, 2-nitro, 4-carbamidylbutane hydrochloride

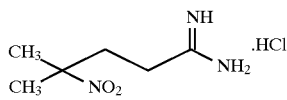

Prepared as in example 1 from 2-Methyl, 2-nitro, 4-cyanobutane to afford the title compound as a white solid. Mass Spectra, M+H=160.

EXAMPLE 27

Acetamidine; Aldrich

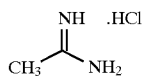

EXAMPLE 28

3-(2-chloro,6-fluorophenyl), 4-carbamidoxime, 5-methylisoxazole; Maybridge Chemical Co. Ltd.

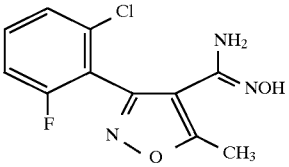

EXAMPLE 29

2-carboxamidoximylthiophene; Boll. sci. fac. chim. ind. Bologna 15(3), 57–62 (1957).

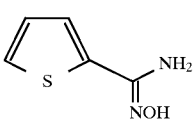

EXAMPLE 30

3-(2,6-dichlorophenyl), 4-carbamidoxime, 5-methylisoxazole; Maybridge Chemical Co. Ltd.

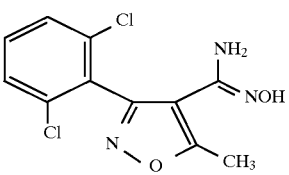

EXAMPLE 31

5-carboxamidoximylisoxazole; Maybridge Chemal Co. Ltd.

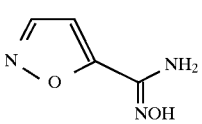

EXAMPLE 32

3,5-bistrifluoromethyl-styrylcarboxamidoxime; Maybridge Chemical Co. Ltd.

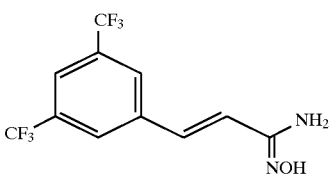

EXAMPLE 33 t-Butylsulfonylacetamidoxime; Maybridge Chemical Co. Ltd.

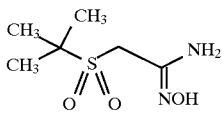

EXAMPLE 34

Phenylacetamidoxime; Aldrich

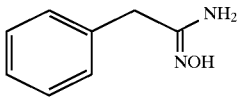

EXAMPLE 35

Formamidoxime; Aldrich

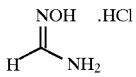

Biological Data

The activity of the above listed compounds as NO synthase inhibitors has been determined in the following assays:

Citrulline Assay for Nitric Oxide Synthase

Nitric oxide synthase activity was measured by monitoring the conversion of [3H]-arginine to [3H]-citrulline. Mouse inducible nitric oxide synthase (miNOS) was prepared from an extract of LPS-treated RAW 264.7 cells and partially purified by DEAE-Sepharose chromatography. Rat brain constitutive nitric oxide synthase (rnNOS) was preparedfrom an extract of rat cerebellum and partially purified by DEAE-Sepharose chromatography. Enzyme and inhibitors were incubated at 37° C. for 15 minutes in a reaction volume of 100 µL with the following components added to start the reaction: 50 mM Tris (pH 7.6), 1 mg/ml bovine serum albumin, 1 mM DTT, 2 mM CaCl2, 10 µM FAD, 10 µM tetrahydrobiopterin, 30 µM L-arginine containing L-[2,3-3H]-arginine at 300 cpm/pmole and 1 mM NADPH. For constitutive NOS, 50 nM calmodulin was also added. The reaction was terminated by addition of cold stop buffer containing 10 mM EGTA, 100 mM HEPES, pH 5.5 and 1 mM citrulline. [3H]-Citrulline was separated by chromatography on Dowex 50W X-8 cation exchange resin and radioactivity determined with a liquid scintillation counter.

Raw Cell Nitrite Assay

RAW 264.7 cells are plated to confluency on a 96-well tissue culture plate grown overnight (17 h) in the presence of LPS to induce NOS. A row of 3–6 wells were left untreated and served as controls for subtraction of nonspecific background. The media was removed from each well and the cells are washed twice with Krebs-Ringers-Hepes (25 mM, pH 7.4) with 2 mg/ml glucose. The cells are then placed on ice and incubated with 50 µL of buffer containing L-arginine (30 µM) +/- inhibitors for 1 h. The assay is initiated by warming the plate to 37° C. in a water bath for 1 h. Production of nitrite by intracellular iNOS is linear with time. To terminate the cellular assay, the plate of cells is placed on ice and the nitrite-containing buffer removed and analyzed for nitrite using a previously published fluorescent determination for nitrite. All values are the average of triplicate wells and are compared to a background-subtracted induced set of cells (100% value).

TABLE I

| Compound | iNOS IC$_{50}$ [µM] | cNOS | Raw Cell IC$_{50}$ [µM] |
|---|---|---|---|
| Example 1 | 39% @10 µM | | |
| Example 2 | 2.3 | 10 | 46 |
| Example 3 | 27 | 31 | |
| Example 4 | 2.0 | 7.3 | |
| Example 5 | 16 | 44 | |
| Example 6 | 39% @10 µM | | |
| Example 7 | 35% @10 µM | | |
| Example 8 | 1.0 | 1.3 | 7.0 |
| Example 9 | 3.0 | 3.0 | 158 |
| Example 10 | 33% @10 µM | | |
| Example 11 | 2.0 | 7.0 | 60 |
| Example 12 | 35% @10 µM* | 26% @10 µM | |
| Example 13 | 43% @100 µM* | 35% @100 µM** | |
| Example 14 | 0% @100 µM* | 0% @100 µM** | |
| Example 15 | 0% @100 µM* | 51% @100 µM** | |
| Example 16 | 2% @100 µM* | 65% @100 µM** | |
| Example 17 | 10% @100 µM* | 0% @100 µM** | |
| Example 18 | 74% @10 µM* | 45% @10 µM** | |
| Example 19 | 30% @100 µM* | 18% @100 µM** | |
| Example 20 | 0% @100 µM* | 0.4% @100 µM** | |
| Example 21 | 18% @100 µM* | 80% @100 µM** | |
| Example 22 | 7% @100 µM* | 1% @100 µM** | |
| Example 23 | 57% @100 µM* | 22% @100 µM** | |
| Example 24 | 0% @100 µM* | 0% @100 µM** | |
| Example 25 | 1% @100 µM* | 0% @100 µM** | |
| Example 26 | 10% @100 µM* | 2% @100 µM** | |

*hiNOS Data
**hecNOS Data

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of inhibiting nitric oxide synthesis in a subject in need of such inhibition by administering a therapeutically effective amount of a compound having the formula:

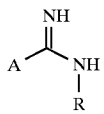

and pharmaceutically acceptable salts thereof, wherein
A is hydrogen, lower alkyl group, lower alkenyl group, lower alkynyl group, alkylthioalkyl group, alkyloxyalkyl group, alkylsulfonylalkyl group, cycloalkyl group, bicycloalkyl group, cycloalkenyl group, cycloalkylalkyl group, phenylalkyl group, phenylalkenyl group, biphenylalkyl group, heterocyclic group, biaryl group, aryl group, or aryl substituted heterocyclic group, wherein each group may be substituted by one or more of substituents selected from the group consisting of alkyl, alkoxy, hydroxy, halogen, nitro, cyano, haloalkyl, carboxylic, carboxamide, amino, alkylamino and dialkylamino; and
R is H, OH or lower alkyl group
with the proviso that when A is phenyl or phenylalkyl, it cannot be substituted with hydroxy.

2. The method of inhibiting nitric oxide synthesis as recited in claim 1 wherein A is hydrogen, lower alkyl group of 1 to 10 carbon atoms, lower alkenyl group of 2 to 6 carbon atoms, lower alkynyl group of 2 to 6 carbon atoms, alkylthioalkyl group of 2 to 6 carbon atoms, alkyloxyalkyl of 2 to 6 carbon atoms, alkylsulfonylalkyl group of 2 to 6 carbon atoms, cycloalkyl group of 3 to 8 carbon atoms, bicycloalkyl group of 6 to 10 carbon atoms, cycloalkenyl group of 3 to 8 carbon atoms, cycloalkylalkyl group of 4 to 10 carbon atoms, phenylalkyl group, phenylalkenyl group, biphenylalkyl group, heterocyclic group, or aryl substituted heterocyclic group, wherein each group may be substituted by one or more of the substituents selected from the group consisting of lower alkyl of 1 to 4 carbon atoms, alkoxy of 1 to 4 carbon atoms, hydroxy, halogen, nitro, cyano, haloalkyl, carboxyl, carboxamide, amino, monoalkylamino or dialkylamino; and R is H, OH or lower alkyl group of 1 to 6 carbon atoms.

3. The method of inhibiting nitric oxide synthesis as recited in claim 1 wherein A is lower alkyl group of 2 to 10 carbon atoms, lower alkenyl group of 2 to 6 carbon atoms, cycloalkyl group of 3 to 8 carbon atoms, bicycloalkyl group of 7 carbon atoms, alkylthioalkyl group of 2 to 6 carbon atoms, alkyloxyalkyl of 2 to 6 carbon atoms, alkylsulfonylalkyl group of 2 to 6 carbon atoms, heterocyclic group, or aryl substituted heterocyclic group, wherein each group may be be substituted by one or more of the substituents selected from the group consisting of lower alkyl, alkoxy, haloalkyl, halogen, and nitro; and R is H OH or lower alkyl group of 1 to 6 carbon atoms.

4. The method of inhibiting nitric oxide synthesis as recited in claim 1 wherein the compound is selected from the group consisting of cyclopropylcarbamidine; isopropylcarbamidine; 1-propylcarbamidine; ethylcarbamidine; 2-methoxyacetamidine; 3-amidinopyridine; 2-amidinothiophene; 2-amidinofuran; 2-chloroacetamidine, 2-methylmercaptoacetamide, Isobutylcarbamidine hydrochloride, Benzylthioacetamidine hydrochloride, Heptadecylcarbamidine hydrochloride, Undecylcarbamidine hydrochloride, 1-Bromo-6-carbamidylhexane hydrochloride, 1-Chloro-4abamidylbutane hydrochloride, 2-Carbamidyl-3-bromothiophene hydrochloride, 2-Amidyl, 3,4-dimethyl, 5-carbamidylthiophene hydrochloride, Styrylcarbamidine hydrochloride, 2-carbamidylnorbornane hydrochloride, 2-Chloro-5-carbamidylnorbornane hydrochloride, 2-Phenylbutyramidine hydrochloride, 2,6-Dimethyl, 7-carbamidylhepta-2-6-diene hydrochloride, 2-Methyl, 2-nitro, 4-carbamidylbutane hydrochloride, Acetamidine, 3-(2-chloro,6-fluorophenyl), 4 carbamidoxime, 5-methylisoxazole, 2-carboxamidoximylthiophene, 3-(2,6-dichlorophenyl), 4-carbamidoxime, 5-methylisoxazole, 5-carboxamidoximylisoxazole, 3,5-bistrifluoromethylstylylcarboxamidoxime, t-Butylsulfonylacetamidoxime, Phenylacetamidoxime, and Formamidoxime.

5. A method of selectively inhibiting nitric oxide synthesis produced by inducible NO synthase over nitric oxide produced by the constitutive forms of NO synthase in a subject in need of such selective inhibition by administering a therapeutically effective amount of a compound having the formula:

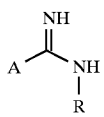

and pharmaceutically acceptable salts thereof, wherein

A is hydrogen, lower alkyl group, lower alkenyl group, lower alkynyl group, alkylthioalkyl group, alkyloxyalkyl group, alkylsulfonylalkyl group, cycloalkyl group, bicycloalkyl group, cycloalkenyl group, cycloalkylalkyl group, phenylalkyl group, phenylalkenyl group, biphenylalkyl group, heterocyclic group, biaryl group, aryl group, or aryl substituted heterocyclic group, wherein each group may be substituted by one or more of substituents selected from the group consisting of alkyl, alkoxy, hydroxy, halogen, nitro, cyano, haloalkyl, carboxylic, carboxamide, amino, alkylamino and dialkylamino; and R is H, OH or lower alkyl group with the proviso that when A is phenyl or phenylalkyl, it cannot be substituted with hydroxy.

6. The method as recited in claim 5 wherein

A is hydrogen, lower alkyl group of 1 to 10 carbon atoms, lower alkenyl group of 2 to 6 carbon atoms, lower alkynyl group of 2 to 6 carbon atoms, alkylthioalkyl group of 2 to 6 carbon atoms, alkyloxyalkyl of 2 to 6 carbon atoms, alkylsulfonylalkyl group of 2 to 6 carbon atoms, cycloalkyl group of 3 to 8 carbon atoms, bicycloalkyl group of 6 to 10 carbon atoms, cycloalkenyl group of 3 to 8 carbon atoms, cycloalkylalkyl group of 4 to 10 carbon atoms, phenylalkyl group, phenylalkenyl group, biphenylalkyl group, heterocyclic group, or aryl substituted heterocyclic group, wherein each group may be be substituted by one or more of the substituents selected from the group consisting of lower alkyl of 1 to 4 carbon atoms, alkoxy of 1 to 4 carbon atoms, hydroxy, halogen, nitro, cyano, haloalkyl, carboxyl, carboxamide, amino, monoalkylamino and dialklamino; and R is H, OH or lower alkyl group of 1 to 6 carbon atoms.

7. The method as recited in claim 5 wherein

A is lower alkyl group of 2 to 10 carbon atoms, lower alkenyl, group of 2 to 6 carbon atoms, cycloalkyl group of 3 to 8 carbon atoms, bicycloalkyl group of 7 carbon atoms, alkylthioalkyl group of 2 to 6 carbon atoms, alkyloxyalkyl of 2 to 6 carbon atoms, alkylsulfonylalkyl group of 2 to 6 carbon atoms heterocyclic group, or aryl substituted heterocyclic group, wherein each group may be be substituted by one or more of the substituents selected from the group consisting of lower alkyl, alkoxy, haloallyl, halogen, and nitro; and R is X, OH or lower alkyl group of 1 to 6 carbon atoms.

8. The method of inhibiting nitric oxide synthesis as recited in claim 5 wherein the compound is selected from the group consisting of: cyclopropylcarbamidine; isopropylcarbamidine; 1-propylcarbamidine; ethylcarbamidine; 2-methoxyacetamidine; 3-amidinopyridine; 2-amidinothiophene; 2-amidinofuran; 2-chloroacetamidine 2-Methylmercaptoacetamide, Isobutylcarbamidine hydrochloride, Benzylthioacetamidine hydrochloride, Heptadecylcarbamidine hydrochloride, Undecylcarbamidine hydrochloride, 1-Bromo-6-carbamidylhexane hydrochloride, 1-Chloro-4-carbamidylbutane hydrochloride, 2-Carbamidyl-3-bromothiophene hydrochloride, 2-Amidyl, 3,4-dimethyl, 5-carbamidylthiophene hydrochloride, Styrylcarbamidine hydrochloride, 2-carbamidylnorbornane hydrochloride, 2-Chloro-5-carbamidylnorbornane hydrochloride, 2-Phenylbutyramidine hydrochloride, 2,6-Dimethyl, 7-carbamidylhepta-2-6-diene hydrochloride, 2-Methyl, 2-nitro, 4-carbamidylbutane hydrochloride, Acetamidine, 3-(2-chloro,6-fluorophenyl), 4-carbamidoxime, 5-methylisoxazole, 2-carboxamidoximylthiophene, 3-(2,6-dichlorophenyl), 4-carbamidoxime, 5-methylisoxazole, 5-carboxamidoximylisoxazole, 3,5-bistrifluoromethylstyrylcarboxamidoxime, t-Butylsulfonylacetamidoxime, Phenylacetamidoxime, and Formamidoxime.

9. A method of lowering nitric oxide levels in a subject in need of such by administering a therapeutically effective amount of a compound having the formula:

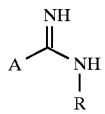 (I)

and pharmaceutically acceptable salts thereof, wherein

A is hydrogen, lower alkyl group, lower alkenyl group, lower alkynyl group, alkylthioalkyl group, alkyloxyalkyl group, alkylsulfonylalkyl group, cycloalkyl group, bicycloalkyl group, cycloalkenyl group, cycloalkylalkyl group, phenylalkyl group, phenylalkenyl group, biphenylalkyl group, heterocyclic group, biaryl group, aryl group, or aryl substituted heterocyclic group, wherein each group may be substituted by one or more of substituents selected from the group consisting of alkyl, alkoxy, hydroxy, halogen, nitro, cyano, haloalkyl, carboxylic, carboxamide, amino, alkylamino and dialkylamino; and R is H, OH or lower alkyl group with the proviso that when A is phenyl or phenylalkyl, it cannot be substituted with hydroxy.

10. The method as recited in claim 9 wherein A is hydrogen, lower alkyl group of 1 to 10 carbon atoms, lower alkenyl group of 2 to 6 carbon atoms, lower alknyl group of 2 to 6 carbon atoms, alkylthioalkyl group of 2 to 6 carbon atoms, alkyloxyalkyl of 2 to 6 carbon atoms, alkylsulfonylalkyl group of 2 to 6 carbon atoms, cycloalkyl group of 3 to 8 carbon atoms, bicycloalkyl group of 6 to 10 carbon atoms, cycloalkenyl group of 3 to 8 carbon atoms, cycloalkylalkyl group of 4 to 10 carbon atoms, phenylalkyl group, phenylalkenyl group, biphenylalkyl group, heterocyclic group, or aryl substituted heterocyclic group, wherein each group may be substituted by one or more of the substituents selected from the group consisting of lower alkyl of 1 to 4 carbon atoms, alkoxy of 1 to 4 carbon atoms, hydroxy, halogen, nitro, cyano, haloalkyl, carboxyl, carboxamide, amino, monoalkylamino and dialkylamino; and R is H, OH or lower alkyl group of 1 to 6 carbon atoms.

11. The method as recited in claim 9 wherein

A is lower alkyl group of 2 to 10 carbon atoms, lower alkenyl group of 2 to 6 carbon atoms, cycloalkyl group of 3 to 8 carbon atoms, bicycloalkyl group of 7 carbon atoms, alkylthioalkyl group of 2 to 6 carbon atoms, alkyloxyallyl of 2 to 6 carbon atoms, alkylsulfonylalkyl group of 2 to 6 carbon atoms heterocyclic group, or aryl substituted heterocyclic group, wherein each group may be substituted by one or more of the substituents selected from the group consisting of lower alkyl, alkoxy, haloalkyl, halogen, and nitro; and R is H, OH or lower alkyl group of 1 to 6 carbon atoms.

12. The method as recited in claim 9 wherein the compound is selected from the group consisting of cyclopropylcarbamidine; isopropylcarbamidine; 1-propylcarbamidine; ethylcarbamidine; 2-methoxyacetamidine; 3-amidinopyridine; 2-amidinothiophene; 2-amidinofuran; 2-chloroacetamidine 2-Methylmercaptoacetamide, Isobutylcarbamidine hydrochloride, Benzylthioacetamidine hydrochloride, Heptadecylcarbamidine hydrochloride, Undecylcarbamidine hydrochloride, 1-Bromo-6-carbamidylhexane hydrochloride, 1-Chloro-4-carbamidylbutane hydrochloride, 2-Carbamidyl-3-bromothiophene hydrochloride, 2-Amidyl, 3,4-dimethyl, 5-carbamidylthiophene hydrochloride, Styrylcarbamidine hydrochloride, 2-carbamidylnorbornane hydrochloride, 2-Chloro-5-carbamidylnorbornane hydrochloride, 2-Phenylbutyramidine hydrochloride, 2,6-Dimethyl, 7-carbamidylhepta-2-6-diene hydrochloride, 2-Methyl, 2-nitro, 4-carbamidylbutane hydrochloride, Acetamidine, 3-(2-chloro,6-fluorophenyl), 4carbamidoxime, 5-methylisoxazole, 2-carboxamidoximylthiophene, 3-(2,6-dichlorophenyl), 4-carbamidoxime, 5-methylisoxazole, 5-carboxamidoximylisoxazole, 3,5-bistrifluoromethylstyrylcarboxamidoxime, t-Butylsulfonylacetamidoxime, Phenylacetamidoxime, and Formamidoxime.

* * * * *